United States Patent [19]

Spindler et al.

[11] Patent Number: 5,326,563
[45] Date of Patent: Jul. 5, 1994

[54] NICOTINE COMPOSITIONS

[76] Inventors: Frank R. Spindler, 42 Abang Avenue, Tanah Merah, Queensland, 4129; Bhupat Rawal, Suite 1, Kenmore Village Shopping Centre, Kenmor, QLD, 4069 both of Australia

[21] Appl. No.: 948,500

[22] Filed: Sep. 22, 1992

Related U.S. Application Data

[62] Division of Ser. No. 499,305, May 17, 1990, Pat. No. 5,158,771.

[30] Foreign Application Priority Data

Nov. 19, 1987 [AU] Australia ................... PI5511

[51] Int. Cl.$^5$ ................ A61K 31/465; A24B 15/24
[52] U.S. Cl. ................ 424/197.1; 424/449;
131/270; 131/347; 131/356; 514/813
[58] Field of Search ............ 131/270, 347, 356;
424/197.1, 449; 514/813

[56] References Cited

U.S. PATENT DOCUMENTS

| | | | |
|---|---|---|---|
| 2,805,667 | 9/1957 | von Bethmann | 131/140 |
| 3,717,155 | 2/1973 | Jacin et al. | 131/17 AC |
| 3,870,794 | 3/1975 | Hutchinson et al. | 242/264 |
| 4,215,706 | 8/1980 | Larson et al. | 131/143 |
| 4,597,961 | 7/1986 | Etscorn | 424/28 |
| 4,821,745 | 4/1989 | Rosen et al. | 131/270 |

FOREIGN PATENT DOCUMENTS

| | | |
|---|---|---|
| 80483/87 | 5/1988 | Australia . |
| 15349/88 | 11/1988 | Australia . |
| 2030862 | 4/1980 | United Kingdom . |
| 2133691 | 8/1984 | United Kingdom . |

OTHER PUBLICATIONS

SU, 301148, Besserezhnov) Jun. 24, 1971 abstract. *Soviet Inventions Illustrated*, Jan. 1971, issued Jan. 1972, Section Ch: Chemical, Part 5 General Organic Chemistry-p. 22, published 1972, Derwent Pub. Ltd., London.

*Primary Examiner*—Thurman K. Page
*Assistant Examiner*—James M. Spear
*Attorney, Agent, or Firm*—Foley & Lardner

[57] ABSTRACT

A composition is provided for use in the suppression of a smoking habit, containing a tobacco plant extract which includes between 0.1% and 8.0% of nicotine and at least one additional tobacco derivative in a water based solvent.

11 Claims, No Drawings

NICOTINE COMPOSITIONS

This application is a division of application Ser. No. 07/499,305, filed May 17, 1990, now U.S. Pat. No. 5,158,771.

FIELD OF INVENTION

This invention relates to a composition having application in assisting cigarette smokers to abandon their habit.

BACKGROUND OF THE INVENTION

Conventionally, the top leaves of the tobacco plant are harvested at an appropriate time and these are cured and processed for use by smokers. The maturing of leaves, and the temperatures during smoking, generate many different and harmful chemicals. Smoking cigarettes has been linked with lung cancer, cardiovascular diseases, etc. There are many proposals by which those who smoke may he assisted to avoid their habit, hut none are universally effective.

OBJECT OF THE INVENTION

It is an object of the present invention to provide a composition which may be utilised by persons who require the stimulus that is the motivation for smoking without the risks attendant to smoking. Other objects, and various advantages of the present invention will hereinafter become apparent.

In the production of smoking tobacco, and cigarettes therefrom, there results a product which incorporates a range of harmful chemicals that arise in the degradation processes undergone by the cut leaves during curing. The range of harmful chemicals is increased by the action of heat in the smoking process. The nicotine which the smoker craves is present in the tobacco leaves at the outset. It is not a product of maturation, curing or combustion, etc and it is these steps that need to be avoided. Typically, the present invention utilises sources such as tobacco leaves so as to generate a product whereby the user may obtain the object of smoking without undergoing the harmful side effects.

OUTLINE OF THE INVENTION

The invention provides a composition for use in the suppression of a smoking habit by dermal application of a tobacco suspension comprising between 0.1% and 8.0% of nicotine in a water based solvent.

The above composition for use in the suppression of a cigarette smoking habit may be provided in a roll-on container.

In methods for production of the above composition, dried but not cured or fresh picked tobacco leaves are utilised to produce the composition.

PREFERRED EMBODIMENTS OF THE INVENTION

The invention achieves its objects by provision of a liquid composition comprising a nicotine solution which may be applied to the user's skin, whereat, components within the composition, including nicotine, may be taken up by the body by a process of absorption.

The invention also provides a method of producing a tobacco composition by extracting nicotine from tobacco plants wherein:

tobacco leaves are mashed;

the mashed leaves are mixed with an aqueous. solvent; and the resulting liquid is decanted and filtered.

The dermal application is preferably achieved by use of a roll-on type applicator. The nicotine, in a liquid solution applied dermally from such a container, is readily taken up by the user through the skin.

In utilising tobacco leaves as a raw material for the composition, production is preferably performed upon the leaves soon after picking so as to lessen the amount of harmful degradation products. It is possible to process liquified plant materials so as to reduce or remove particular harmful components, and that way provide a product with greatly reduced concentrations of the chemical compounds that are being inhaled by cigarette smokers. By picking selected parts of the tobacco plant at selected times, and selectively processing the raw material, it is possible to generate a liquid tobacco composition ,that comprises a reduced range of harmful chemicals, by partial or complete removal, which when applied dermally poses none of the health problems facing smokers.

In a preferred embodiment the invention proposes to use tobacco leaves to generate a composition that retains the natural attributes of the plant; nicotine; proteins, chlorophylis; and several enzymes. Both these latter compounds are known to overcome carcinogenic effect of known carcinogens. On analysis of the green leaves of the tobacco plant that are utilised, uncured, in the process described below, it is revealed that they contain benzo (a) pyrene, a known carcinogen, but only in trace amounts, unlike mature tobacco. Thus it is preferred to use the uncured tobacco to develop a liquid composition to be used in the manner laid out herein. The process further dilutes this carcinogen.

In order to outline the invention in greater detail, the following examples are presented to illustrate the manner in which preferred compositions are produced.

In a first process, selected leaves of tobacco plants are harvested and processed in an uncured state, the leaves being processed as soon after harvesting as is practical so as to minimise the generation of harmful products as the leaves degrade. These leaves are mashed and combined with an aqueous solvent. The mixture is best agitated, by shaking etc. The aqueous solvent may be purified water, with or without chlorine which serves to reduce benzo (a) pyrenes. The pH of this solvent may be adjusted between 3.0 and 14.0.

The combining of the mash with an aqueous solvent may be carried out at temperatures between 2 and 150° C., depending on the quality of the tobacco. After cooling, the liquid is decanted and filtered.

The output of the above process may be formulated with a preservative, and it is bottled in a roll-on or other suitable container for dermal application.

In a second process, tobacco leaves are picked from the middle to the top of the plant, not less than seven days from their being topped, and they are processed within 24 hours of harvesting. The leaves are used as picked, or they may be dried at not more than 160° C. before processing. The leaves are liquified in a chlorinated aqueous solution with a pH range between 3.0 to 14 so as to obtain a slurry of liquid tobacco. The aqueous phase is separated and the above steps are repeated a number of times with fresh leaves and the volume made up with fresh solvent.

Where chlorinated aqueous solvents are proposed above, other aqueous solvents might be utilised. What may be suitable here will be determined by the dual requirement for enabling separation of the useful components from the mash and, if the solvent is to remain in the end product, for application to skin without causing complications.

The above processes provide a liquified tobacco that can be used for the purpose of reducing the amount of cigarettes smoked by the dermal application of the liquified tobacco. The liquified tobacco or an aqueous solution of nicotine can be combined with a deodorant type roll-on for transdermal self administration of nicotine for the purpose of reducing smoking.

Typical features of the liquified tobacco are as follows:

1) Contains only parts per billion of known carcinogenic substances because carcinogens are typical only of cured tobacco and are not typical of green tobacco.

2) Contains all natural organic substances and does not contain substances achieved by curing. The invention, in its preferred form, is a tobacco plant extract comprised of soluble plant components, including nicotine, with carcinogenic components reduced in concentration, or totally removed. The nicotine may be derived from different parts of the tobacco plant such as leaves, roots, stems, or the liquids contained therein.

The above described solutions are able to be applied dermally from a roll-on with a greater control over dosage than might be achieved by other methods of application.

We claim:

1. A composition for use in the suppression of a smoking habit by dermal application comprising a tobacco plant extract which comprises between 0.1% and 8.0% of nicotine and at least one additional tobacco derivative in a water based solvent, wherein said tobacco plant extract is obtained from tobacco leaves which have been processed after harvesting within about 24 hours so as to minimize the development of degradation products in said tobacco leaves, and wherein said at least one additional tobacco derivative is soluble in said solvent.

2. A composition as claimed in claim 1, wherein said at least one additional tobacco derivative is selected from the group consisting of chlorophylls and tobacco leaf enzymes.

3. A composition as claimed in claim 2, further comprising a preservative.

4. A container for use in the suppression of a cigarette smoking habit having a quantity of the composition of claim 14 therein for dermal application.

5. A composition as claimed in claim 1, wherein said tobacco plant extract is extracted from tobacco leaves selected from the group consisting of dried but not cured and fresh picked tobacco leaves.

6. A method for suppressing a smoking habit which comprises the step of applying to the skin of a person having a smoking habit a composition as claimed in claim 1.

7. A composition according to claim 1, wherein said composition comprises only parts per billion of benzo (a) pyrene.

8. A composition according to claim 1, wherein said composition comprises no carcinogenic components.

9. A composition according to claim 1, wherein said nicotine is derived from parts of the tobacco plant selected from one or more of the leaves, roots, stems and the liquids contained therein.

10. A composition for use in the suppression of a smoking habit by dermal application comprising a tobacco plant extract which comprises between 0.1% and 8.0% of nicotine and at least one additional tobacco derivative in a water based solvent, wherein said at least one additional tobacco derivative is soluble in said solvent and is selected from the group consisting of chlorophylls and tobacco leaf enzymes.

11. A composition for use in the suppression of a smoking habit by dermal application comprising a tobacco plant extract which comprises between 0.1% and 8.0% of nicotine and at least one additional tobacco derivative in a water based solvent, wherein said at least one additional tobacco derivative is soluble in said solvent, and wherein said composition comprises only parts per billion of benzo (a) pyrene.

* * * * *